US011419655B2

(12) United States Patent
Aryan (10) Patent No.: US 11,419,655 B2
(45) Date of Patent: Aug. 23, 2022

(54) INTRAOPERATIVE MONITORING AND SCREW PLACEMENT APPARATUS

(71) Applicant: Henry E. Aryan, Fresno, CA (US)

(72) Inventor: Henry E. Aryan, Fresno, CA (US)

( * ) Notice: Subject to any disclaimer, the term of this patent is extended or adjusted under 35 U.S.C. 154(b) by 323 days.

(21) Appl. No.: 16/853,392

(22) Filed: Apr. 20, 2020

(65) Prior Publication Data

US 2021/0322079 A1 Oct. 21, 2021

(51) Int. Cl.
*A61B 17/88* (2006.01)
*A61B 5/389* (2021.01)
*A61B 17/00* (2006.01)

(52) U.S. Cl.
CPC .......... *A61B 17/8891* (2013.01); *A61B 5/389* (2021.01); *A61B 2017/00039* (2013.01); *A61B 2562/0261* (2013.01)

(58) Field of Classification Search
CPC ................ A61B 17/8891; A61B 5/389; A61B 2017/00039; A61B 2562/0261; A61B 17/7076; A61B 17/8875; A61B 2017/00199; A61B 2017/00398; A61B 2017/0046; A61B 2017/00876; A61B 2090/066; H01R 39/08; H01R 39/24
See application file for complete search history.

(56) References Cited

U.S. PATENT DOCUMENTS

| 5,474,558 | A | 12/1995 | Neubardt |
| 5,898,112 | A | 4/1999 | Dawood |
| 8,774,911 | B2 | 7/2014 | Buono |
| 8,932,302 | B2 | 1/2015 | Jimenez |
| 11,317,973 | B2 * | 5/2022 | Calloway .............. H04N 5/2354 |
| 2005/0221654 | A1 * | 10/2005 | Phillips ............... H01M 50/209 439/347 |

(Continued)

FOREIGN PATENT DOCUMENTS

WO WO2009105106 A2 8/2009

OTHER PUBLICATIONS

Deletis, V., Basic Methodological Principles of Multimodal Intraoperative Monitoring During Spine Surgeries, Eur Spine J, May 7, 2007, pp. 147-152.

(Continued)

*Primary Examiner* — David D Davis
(74) *Attorney, Agent, or Firm* — GSS Law Group; Gregory Scott Smith; Phillip M. Wagner (57) ABSTRACT

An intraoperative monitoring module (IMM) for assessing strength of screw attachments to bone and detecting breaches includes a torque sensor on a rotatable tool receptacle and a variable-output current source. The IMM provides concurrent monitoring of rotational torque applied to a screw and stimulus current passing through the screw into bone for evoked electromyography. A motor housing configured to drive in rotation a tool receptacle on the IMM, a screw driver modified for carrying the stimulus current, and a screw attached to the screw driver are optionally included. Cooperative anti-rotation features on the motor housing and IMM support accurate torque measurements and prevent the outer housing of the IMM from rotating with the tool receptacle while a screw is being driven. The motor housing optionally provides electrical power to the IMM.

16 Claims, 10 Drawing Sheets

(56) References Cited

U.S. PATENT DOCUMENTS

| | | | |
|---|---|---|---|
| 2008/0215056 A1* | 9/2008 | Miller | A61B 17/32002 606/80 |
| 2013/0090698 A1 | 4/2013 | Nuckley | |
| 2015/0157321 A1* | 6/2015 | Zergiebel | H01R 39/08 227/175.1 |
| 2015/0317894 A1* | 11/2015 | Chen | B60C 29/06 340/665 |
| 2015/0374366 A1* | 12/2015 | Zergiebel | F16H 25/20 74/89.23 |
| 2015/0374370 A1* | 12/2015 | Zergiebel | A61B 17/072 439/78 |
| 2017/0043462 A1* | 2/2017 | Brebant | B60C 23/0494 |
| 2018/0317979 A1 | 11/2018 | Gdowski | |
| 2020/0038084 A1* | 2/2020 | Brown | A61B 17/1626 |
| 2022/0123581 A1* | 4/2022 | Clarke | H01M 10/44 |
| 2022/0140411 A1* | 5/2022 | Clarke | G01R 31/3835 320/124 |

OTHER PUBLICATIONS

Bolger, C. et al., Electrical Conductivity Measurement: A New Technique to Detect Iatrogenic Initial Pedicle Perforation; Eur Spine J, 16:1919-1924.

Muftah, M. et al., An Improved Strain Gauge-Based Dynamic Torque Measurement Method, Int J Circuits, Issue 1 vol 7 2013, pp. 66-73.

DID-4A Digital Torque Screwdriver, author and original publication date unknown, internet web page at address https://gaugecity.com/products/did-4a-digital -torque-screwdriver.

Mozhanova, M., Design of a High Resolution Surface Electromyogram (EMG) Conditioning Circuit, Jan. 4, 2012, Worcester Polytechnic Institute.

Gupta, K. et al., Changes in Electrical Properties of Bones as a Diagnostic Tool for Measurement of Fracture Healing, Hard Tissue, Jan. 21, 2013 (1) 3.

Spineguard DSG Technology, authors and original publication date unknown, Intenet web pages at address https://www.spineguard.com/dynamic-surgical-guidance-technology.

Electric Orthopedic Screwdriver With Torque Monitor, author and original publication date unknown, Internet web pages at address https://www.medicalexpo.com/prod/biomet/product-74862-695119.html.

* cited by examiner

Fig. 7 CROSS-SECTION A - A

INTRAOPERATIVE MONITORING AND SCREW PLACEMENT APPARATUS

FIELD OF THE INVENTION

Embodiments are related to surgical devices and more particularly to devices for placing threaded fasteners in bone.

BACKGROUND

Healthy intervertebral discs serve as cushions between vertebrae and allow flexing and bending of the vertebral column. Degenerative disc disease related to the deterioration of intervertebral discs and adjacent vertebrae may lead to pain, impaired range of motion, weakness, numbness, and other undesirable effects. Deterioration of discs or vertebrae may occur as a result of trauma, the natural effects of aging, or other causes. Some examples of degenerative disc disease include formation of bone spurs and neurological injury from material from a herniated disc intruding into the spinal canal.

Treatment for degenerative disc disease may involve removal of a degenerated disc and/or spurs and fusing the vertebra together. Plates and other devices may be attached to the vertebra with screws to hold the vertebra in correct position until fusion takes place. Screws are preferably fixed strongly in bone to provide stable positioning of the bone and avoid damage to the bone and other tissues. The strength of screw fixation in bone is important in determining success of surgery and influences post-operative management. However, bone may be weakened by illness, age, osteoporosis, and other factors, possibly reducing the strength of attachment of a screw to the bone. It is therefore desirable to predict the ability of bone to provide a stable, secure attachment for a screw along a selected screw insertion path.

The ability of bone to provide stable support for a screw has been predicted and assessed by pre-operative and intraoperative methods. For example, pre-operative imaging techniques such as bone scans may give insight into bone quality for screw placement. Imaging has also been used intraoperatively to detect bone quality problems relating to screw placement and advancement, for example bone that is too porous to hold a screw securely, bone that has cracked, split, fractured, eroded, or has other structural damage, breaches of a bone surface by a screw, and so on.

Other methods have been applied to assess bone quality for screw placement. Mechanical properties of bone have been inferred from electrical measurements such as electrical resistance of bone, bone thickness and/or strength as detected by distortion of an electric field emitted from a probe tip, pressure measurements in screw holes drilled along the screw insertion path, and others. Pressure measurements, whether by instrument or the surgeon's sense of touch and experience, may give an indication of bone that is too soft, too porous, fractured, or too hard to support a successful screw placement.

The strength of a screw attachment to bone has been estimated from torque measurements made during screw advancement through bone. Torque measurements may indicate when bone is either too soft or too hard for successful stabilization of a screw advancing through the bone. Attempts have been made to apply torque measurements to detecting a breach of a bone surface by an advancing screw tip. However, torque measurements alone have been found in some cases to give false indications of a breach having occurred or to have missed breaches later detected by imaging.

A screw breaching a bone surface and coming into contact with a nerve may cause pain, impairment of function of the muscle activated by the nerve, and other unwanted effects. Proximity to a nerve of a screw advancing through bone has been observed by detecting a response from the muscle controlled by the nerve, for example by placing a probe in the screw hole drilled in the bone and observing an electromyogram (EMG) response by the muscle receiving signals from a nerve close to the screw hole. Stimulus currents injected through a probe placed in the screw hole have been used in conjunction with EMG monitoring, a technique sometimes referred to as "evoked EMG". Evoked EMG attempts to determine a threshold magnitude of stimulus current at which a muscle response is detected. A detected muscle response at a low value of stimulus current may correlate to a screw having breached, or close to breaching, a surface of bone close to a nerve. An observed muscle response at a higher value of stimulus current may indicate the screw is passing through structurally sound bone with sufficient bone separating the screw from adjacent nerves, i.e. no breach has occurred.

In each of the previous methods, screw placement procedures are delayed or interrupted to make assessments of bone quality and security of screw placement. For example, the screw driver being used to advance the screw into bone may be capable of limiting and/or measuring applied torque, but the advancement of the screw and the torque measurement are both interrupted and the screw disconnected from the screw driver to image the insertion path for assessment of bone quality and determine if a breach is imminent or has already occurred. Similarly, previously available instruments and methods detach the screw from the screw driver before determining a value of bone electrical impedance or a threshold value of stimulus current needed to achieve a muscle response for an evoked EMG.

Previously available instruments have not been capable of making concurrent measurements of torque and evoked EMG response with a screw driver that remains in continuous contact with a screw being driven into bone. Switching back and forth between separate mechanical probes, electrical probes, screw drivers, and measurement devices for assessing bone quality for screw placement, whether by imaging, measurement of electrical properties of bone and/ or muscle response, or measurement of mechanical parameters such as torque and pressure, delays advancing the screw to its final stable position, lengthens the amount of time needed to perform a successful screw placement, increases the possibility of intraoperative and post-surgical complications by the introduction of additional instruments at a surgical site on a patient, and raises the cost of performing surgery.

SUMMARY

An example of an apparatus in accord with an embodiment includes a screw placement tool and an intraoperative monitoring module. The intraoperative monitoring module includes an outer enclosure and a tool receptacle rotatably coupled to the outer enclosure. The tool receptacle includes a tool socket configured for receiving the screw placement tool; a torque sensor affixed to the tool receptacle; and a drive coupling at an end of the tool receptacle opposite the tool socket. The intraoperative monitoring module further includes a variable-output current source; a microcontroller electrically connected to the torque sensor and the variable-output current source; and an optional status display attached to the outer enclosure. The microcontroller is configured to communicate to the status display a value of current output from the variable-output current source and a value of torque determined from an output of the torque sensor. The example apparatus further includes a motor housing configured for attachment to the drive coupling and the outer enclosure of the intraoperative monitoring module. The motor housing is configured for driving the drive coupling in rotation at a selected rate of rotation and in a selected direction of rotation.

Another example apparatus embodiment includes an intraoperative monitoring module and a motor housing. The example intraoperative monitoring module includes an outer enclosure and a tool receptacle rotatably coupled to the outer enclosure. The example tool receptacle includes a tool socket; a torque sensor affixed to the tool receptacle; and a drive coupling at an end of the tool receptacle opposite the tool socket. The example intraoperative monitoring module further includes a variable-output current source; a microcontroller electrically connected to the torque sensor and the current source; and a status display attached to the outer enclosure. The microcontroller is preferably configured to communicate to the status display a value of current output from the current source and a value of torque from the torque sensor. The motor housing is preferably configured for attachment to the drive coupling and to the outer enclosure, and for driving the drive coupling in rotation.

Another example apparatus embodiment includes an intraoperative monitoring apparatus. The intraoperative monitoring apparatus includes an outer enclosure and a tool receptacle rotatably coupled to the outer enclosure. The example tool receptacle includes a tool socket; a torque sensor affixed to the tool receptacle; and a drive coupling at an end of the tool receptacle opposite the tool socket. The example intraoperative monitoring apparatus further includes a variable-output current source electrically connected to a contact pin on the tool receptacle; a microcontroller electrically connected to the torque sensor and the variable-output current source; and a status display attached to the outer enclosure. The microcontroller is preferably configured to communicate to the status display a value of current output from the current source and a value of rotational torque determined from an output of the torque sensor.

DESCRIPTION

An example embodiment of a medical apparatus for secure placement of threaded fasteners in bone is configured for concurrent intraoperative monitoring of torque and generation of stimulus current for evoked EMG while maintaining continuous electrical and mechanical connection to a fastener being advanced into a bone. The example apparatus includes an intraoperative monitoring module (IMM) configured for mechanical and optionally for electrical connection to a motor housing and a screw placement tool. The IMM includes a tool receptacle rotatably coupled to an outer enclosure, a torque sensor for measuring rotational torque acting on the screw placement tool while a screw is being driven in rotation by a motor in the motor housing, and a variable-output current source configured for generating a stimulus current for making evoked EMG measurements. The IMM optionally includes a status display for displaying values relating to torque and EMG monitoring and switches for setting and selecting operational parameters and displayed information. The example medical apparatus optionally includes the screw placement tool. Some apparatus embodiments include the motor housing.

The example medical apparatus is effective for monitoring of torque and stimulus current for evoked EMG concurrently with placement of a screw in bone, without requiring interruption of mechanical and electrical connections to the screw during the placement procedure. The apparatus is further effective for detecting screw breaches with good confidence in breach detection when used in conjunction with an external EMG system, and for assessing the ability of bone along a selected screw placement path to provide stable and secure attachment of a screw. The continuous monitoring and reporting of parameters relating to the structural integrity of bone and the proximity of the screw to neural tissue allows a surgeon to assess bone quality and prospects for a screw breach or neural interference along a selected screw placement path in near real-time, without interrupting contact between the screw driver and the screw being placed. Apparatus embodiments are therefore well suited to continuous monitoring and assessment of bone properties, selection of screw placement locations and screw placement paths, and strength of screw attachments to bone for pedicle screws used in procedures on spinal vertebrae. Apparatus embodiments are also beneficial for monitoring and assessing screw placements in surgical procedures on bones other than spinal vertebrae.

An IMM in accord with an embodiment 100 is optionally provided in a sterile package as a single-use item. An IMM configured as a single-use item is preferably fully functional for the entire duration of a surgical procedure on a single patient, but after the procedure is completed the IMM is not re-used and may be disposed of. An IMM configured as a single-use item optionally includes a non-rechargeable electric storage battery and may have less robust protection against high sterilization temperatures and sanitizing solvents than an IMM configured for use in more than one surgical session.

Figure 1:
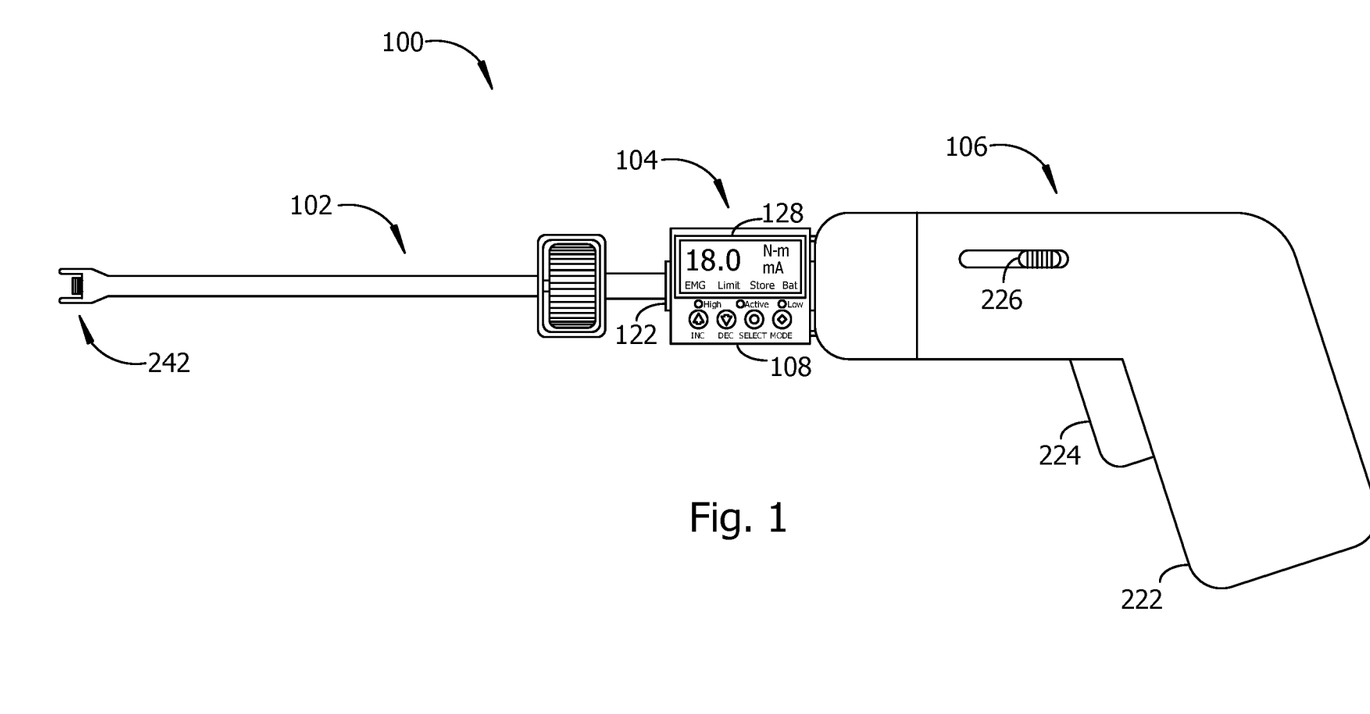
FIG. 1 shows an example apparatus embodiment including an intraoperative monitoring module attached to an optional motor housing and an optional screw placement tool.

An example of an intraoperative monitoring module (IMM) 104 in accord with a medical apparatus embodiment 100 is shown in FIG. 1. The IMM 104 is configured on a side of an outer enclosure 108 for mechanical and electrical connection to an optional screw placement tool 102. The IMM 104 is configured on a side opposite the screw placement tool for connection to an optional motor housing 106. A tool receptacle 122 rotatably coupled to the outer enclosure 108 is configured on a first end to receive the screw placement tool and on an opposite end to connect to the motor housing 106. In an alternative embodiment 100, the outer enclosure 108 of the IMM 104 is an integrally-formed part of the motor housing 106, with the IMM positioned on the motor housing as suggested in the example of FIG. 1. In another alternative embodiment 100, the IMM 104 is an integrally-formed part of the motor housing 106 shown in the example of FIG. 12.

In the example of FIG. 1, the screw placement tool 102 is configured as a screw driver with a screw engaging end 242 arranged for retaining and driving a tulip head screw (not shown). Additional features of the example screw driver for a tulip head screw will be explained later with regard to FIGS. 15, 16, and 17. Other examples of a screw placement tool 102 include, but are not limited to, a screw driver with an end shaped for driving a Philips head screw, a screw driver with an end shaped for driving an Allen head screw, a screw driver with a socketed end shaped for driving a hex head screw, a test probe for injecting EMG stimulus current into a screw hole formed in bone, a drill for forming a screw hole in bone, and a tap for threading a drilled hole.

The example motor housing 106 couples to the IMM to drive the tool receptacle 122 in rotation. The motor housing 106 preferably includes an on/off and speed control switch 224 for controlling a rotation speed of a motor (not illustrated) inside the motor housing and a motor reversal switch 226 for controlling a direction of rotation of the motor to selectively advance or withdraw a screw from a drilled hole. The motor housing 106 preferably receives electrical power for operating the motor from an electric power storage battery (not shown) attached inside the hand grip 222 or alternately attached to the outside of the hand grip or another part of the motor housing.

Depressing the speed control switch 224 on the motor housing preferably rotates the tool receptacle 122 on the IMM 104 without causing rotation of the outer enclosure 108 of the IMM relative to nonrotating parts of the motor housing 106 such as the hand grip 222. Rotation of the tool receptacle 122 turns a screw placement tool 102 retained in the tool receptacle at a rotational speed selected by depressing the speed control switch 224. The tool receptacle, a screw placement tool attached to the tool receptacle, and a screw attached to the screw placement tool rotate together in a direction of rotation selected by the motor reversal switch 226.

Additional features of an IMM 104 in accord with an embodiment 100 are shown in the examples of FIGS. 2-9. The outer enclosure 108 protects components inside the enclosure from mechanical damage and isolates electrical components from exposure to water, biological fluids, and cleaning agents commonly encountered during sanitization of the IMM 104 and use of the IMM in medical procedures. In some embodiments the outer enclosure is liquid resistant, i.e., the enclosure is configured to oppose liquid entry into interior spaces holding electrical components.

The tool receptacle 122 is rotatably coupled to the enclosure 108 from a first side wall 112 of the enclosure to a second side wall 114 opposite the first side wall. The first 112 and second 114 side walls are connected to one another by a third side wall 116, a fourth side wall 118 opposite the third side wall, a front side 110, and a back side 120 opposite the front side. In an alternative embodiment, the outer enclosure is configured as a hollow cylinder with end caps, rather than the approximately rectangular box shown in the example figures, and the tool receptacle is coupled to the end caps. A tool socket 124 for receiving the screw placement tool 102 is formed on the tool receptacle 122 adjacent the first side wall 112. A drive coupling 125 for connecting the tool receptacle 122 to the motor housing 106 is formed on the tool receptacle 122 adjacent the second side wall 114. In the example tool receptacle 122 of FIG. 5, the drive coupling 125 is implemented as a hexagonal socket 126 sized for a sliding fit of a hexagonal drive shaft 233 on some embodiments of the motor housing 106. In the example tool receptacle 122 of FIG. 6, the drive coupling 125 is implemented as a hexagonal post 156 extending outward from the tool receptacle and side wall of the IMM. Some embodiments of the motor housing 106 include clamp jaws 232 for securely holding the hexagonal post 156 in a rotatable chuck 230 driven by the motor in the motor housing.

Anti-rotation features 145 of the IMM 104 and motor housing 106 oppose rotation of the outer enclosure 108 relative to the motor housing when the tool receptacle 122 is driven in rotation. Examples of anti-rotation features 145 include a first anti-rotation pin 144 and an optional second anti-rotation pin 146 extending outward from the second side wall 114 of the outer enclosure 108. The first 144 and second 146 anti-rotation pins are positioned to engage with corresponding pin receptacles 234 formed on a part of the motor housing 106 that does not rotate when the speed control switch 224 is depressed. The pin receptacles 234 are an example of an anti-rotation feature 145 on the motor housing configured to cooperate with anti-rotation features on the IMM to prevent the IMM from rotating when the tool receptacle is driven in rotation by motors in the motor housing. The anti-rotation features of the IMM 104 hold a status display 128 and other components on the front side 110 at a constant viewing angle relative to the hand grip and other stationary parts of the motor housing 106. Other examples of anti-rotation features 145 include, but are not limited to, a bayonet mount with a slotted collar on the outer enclosure positioned to engage a radial pin on the motor housing, a pin extending radially outward from the IMM in a direction perpendicular to the axis of rotation of the tool receptacle engaging a slotted collar on the motor housing, a magnet in the IMM positioned to couple to a magnet in the motor housing, an aperture formed in the IMM positioned to receive a spring-loaded pushbutton on the motor housing, and a threaded ring on the IMM engaging a threaded collar on the motor housing.

Figure 7:
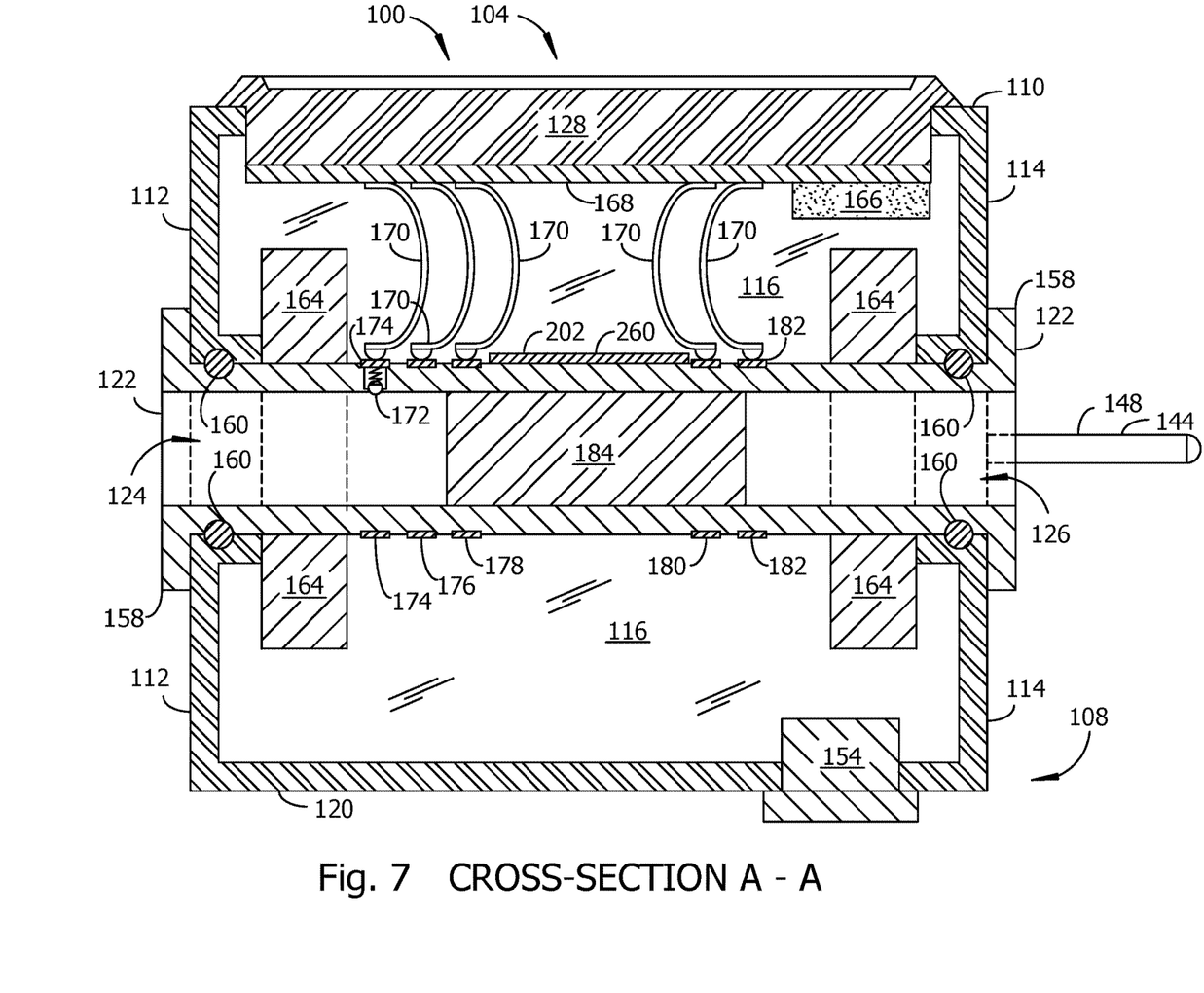
FIG. 7 shows a cross-sectional view A-A of examples of some components included in the intraoperative monitoring module of the previous figures.

Examples of internal features of an IMM 104 are shown in cross-sectional view A-A in FIG. 7. A location and viewing direction for the cross section is marked by a section line labeled A-A in FIG. 4. The tool receptacle 122 is rotatably coupled to the side walls of the outer enclosure 108. The tool receptacle 122 extends from a first side wall 112 to a second side wall 114 through the interior of the outer enclosure 108. Flanges 158 on the tool receptacle prevent the tool receptacle from slipping out of the outer enclosure. Two sealing gaskets 160, one near each end of the tool receptacle, oppose liquid intrusion into the interior of the outer enclosure 108. An O-ring is an example of a sealing gasket 160 suitable for use in an IMM. A sealing gasket may optionally be provided as a circumferential ridge integrally formed on the tool receptacle. Two rotary bearings 164 attached to at least one of the side walls of the outer enclosure 108 support the tool receptacle 122 and reduce frictional losses while the tool receptacle is subjected to rotational torque during placement of screws.

A printed circuit board assembly 168 affixed to a wall of the outer enclosure 108 and/or the status display 128 includes circuits for measuring and monitoring torque and evoked EMG as will be explained in more detail with regard to FIG. 9. In some embodiments 100 the status display 128 and the printed circuit board assembly 168 are provided as separate parts connected by a flat cable and in other embodiments 100 are mechanically and electrically integrated into one assembly. When included in an embodiment 100, the status display 128 is connected for data communication with the microcontroller 208. Examples of a status display 128 include, but are not limited to, a liquid crystal display, a light-emitting diode (LED) display, and an organic LED (OLED) display. In some embodiments the status display is sufficiently flexible to permit attachment to a substantially nonplanar surface of the enclosure 108. Some apparatus embodiments 100 omit the status display 128 from the IMM, instead communicating information to be displayed over a wireless communication transceiver to a remote device such as a smart phone or a computer monitor. An apparatus embodiment 100 including the status display 128 may concurrently display information locally on the status display and remotely on a separate display.

The printed circuit board assembly 128 further includes switches (136, 138, 140, 142) accessible from the front side 110. The switches may be provided as individual switches soldered to the printed circuit board assembly or may alternatively be provided as a membrane switch assembly 143. When included in an embodiment 100, the membrane switch assembly 143 optionally includes snap domes between a switch layer and a graphics layer to provide tactile feedback during switch operation. The membrane switch assembly 143 optionally includes the indicators (130, 132, 134) attached to a switch layer, with the indicators visible when illuminated through an outer layer of the membrane switch assembly. The membrane switch assembly is optionally sealed against liquid intrusion. Components and connections on the printed circuit board assembly, for example a microcontroller, a memory connected for data communication with the microcontroller, and other components shown in FIG. 9, are optionally protected by a conformal coat to resist damage by exposure to water, humidity, cleaning agents, dust, and biological materials.

Spring contacts 170 establish electrical connections between circuits on the printed circuit board assembly and circumferential slip rings on an outer surface 198 of the tool receptacle 122. A separate spring contact 170 is provided for each of a first slip ring 174, a second slip ring 176, a third slip ring 178, a fourth slip ring 180, and a fifth slip ring 182. Each spring contact maintains continuous contact with its corresponding slip ring while the tool receptacle 122 turns through full revolutions. Electrical connections between slip rings and a torque sensor are made with electrical conductors (not shown) positioned on the exterior and interior surfaces of the tool receptacle 122 in such a manner that no two of the slip rings are electrically shorted to one another.

Electrical contact between the first slip ring 174 and a screw placement tool 102 retained in the tool socket 124 of the tool receptacle 122 is established by a spring-loaded contact pin 172 electrically connected to the slip ring 174 and passing into the void space inside the tool socket. A strong permanent magnet 184 attached to, or alternately molded into, the interior of the tool receptacle holds the screw placement tool firmly in position in the tool socket 124. For embodiments of a tool receptacle 122 having a hexagonal socket 126 for receiving a hexagonal drive shaft 233 from the motor housing 106, the permanent magnet 184 inside the tool receptacle, or alternatively a second magnet 184, firmly holds the IMM 104 against the drive shaft 233.

Figure 5:
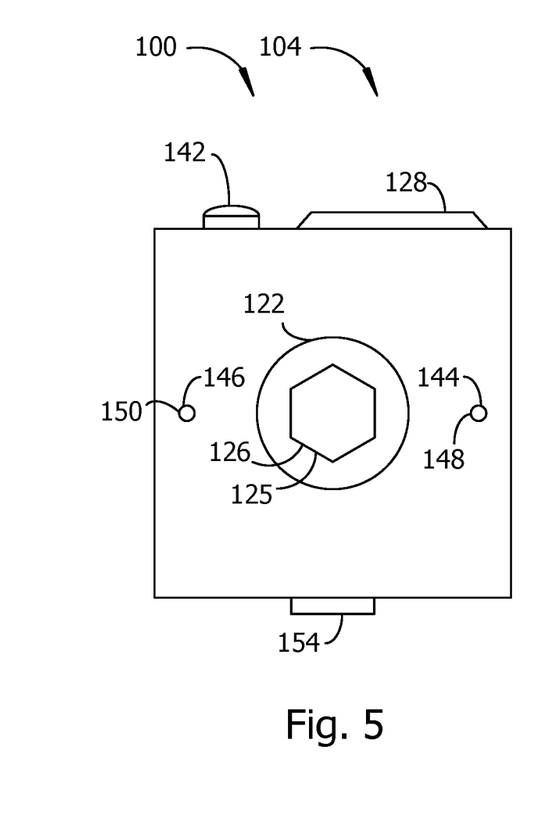
FIG. 5 shows a view toward another side wall of the enclosure for the example intraoperative monitoring module of FIGS. 1-4, further illustrating an example of an end of the tool receptacle having a drive coupling configured for connection to a motor housing.
Figure 6:
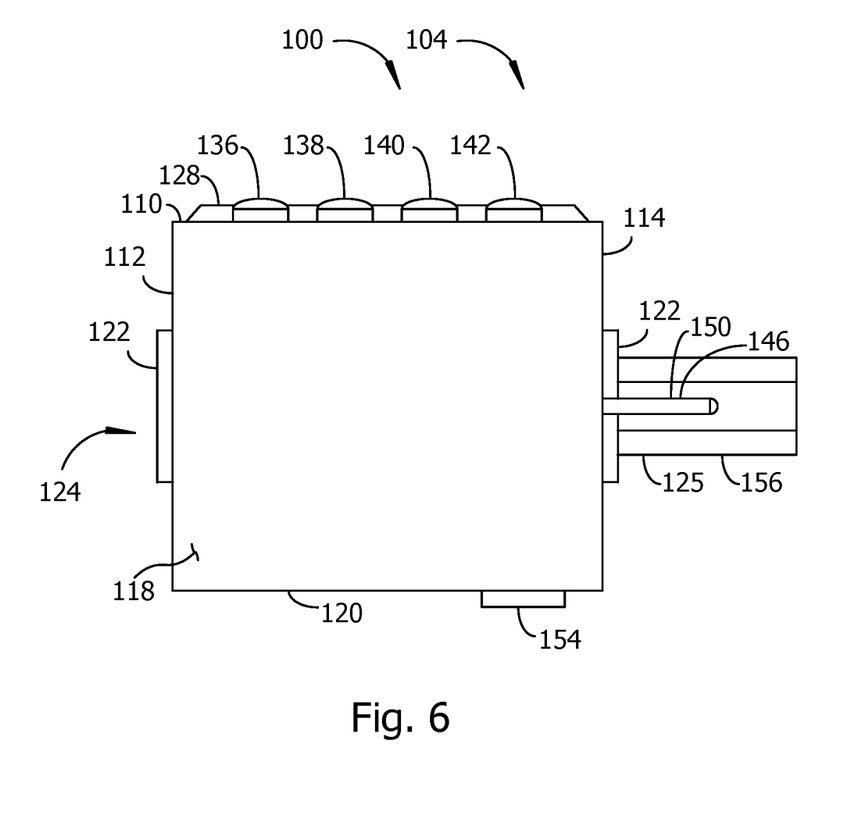
FIG. 6 shows a view toward the side wall of FIG. 3, illustrating an example of the tool receptacle with the drive coupling implemented as a hexagonal post.
Figure 8:
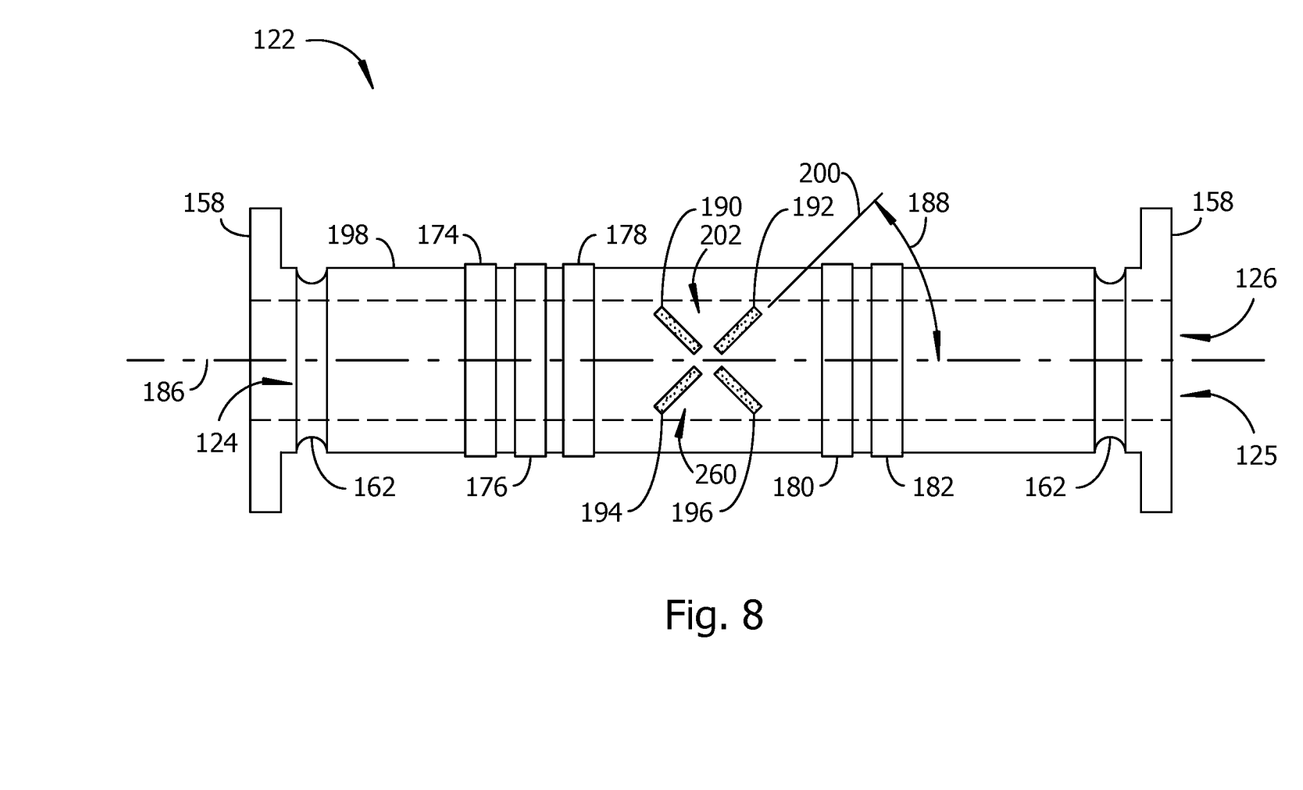
FIG. 8 shows a side view of an example tool receptacle included in the intraoperative monitoring module of the previous figures.

More details of an example tool receptacle are shown in FIG. 8. The tool receptacle 122 may be formed with a hollow cylinder extending from circumferential flanges 158 at an end with a tool socket 124 to an opposite end with circumferential flanges 158 and a drive coupling 125. The drive coupling 125 is implemented in some embodiments 100 as a hexagonal socket 126 as shown in the example of FIG. 5, and in other embodiments as a hexagonal post 156 as shown in the example of FIG. 6. A gasket channel 162 formed in the outer surface 198 near each end of the tool receptacle is positioned to hold a sealing gasket 160. Similar channels for sealing gaskets are optionally formed in the first side wall 112 and second side wall 114 of the outer enclosure 108. The first slip ring 174, second slip ring 176, third slip ring 178, fourth slip ring 180, and fifth slip ring 182 are formed from an electrically conductive material with low electrical resistance and are attached to the outer surface 198, extending without interruption all the way around the outer surface.

Torque applied to a tool receptacle 122 retained in the tool socket 124 is measured by a torque sensor 260 attached to the tool receptacle. The torque sensor 260 includes a strain gauge bridge 202 strongly attached to the outer surface 198. The strain gauge bridge includes a first strain gauge 190 and a second strain gauge 192 and optionally includes a third strain gauge 194 and a fourth strain gauge 196. A primary strain-sensing axis 200 for each strain gauge is preferably oriented at an angle 188 of 45 degrees to the central rotational axis 186 of the tool receptacle 122. In some embodiments 100, all four strain gauges are attached to the outer surface 198 in close proximity to one another. In other example embodiments 100, the first strain gauge 190 and second strain gauge 192 are attached to the outer surface 198

180 degrees away from the third strain gauge 194 and fourth strain gauge 196, i.e., at opposite ends of a diameter of the cylindrical outer surface 198.

Figure 9:
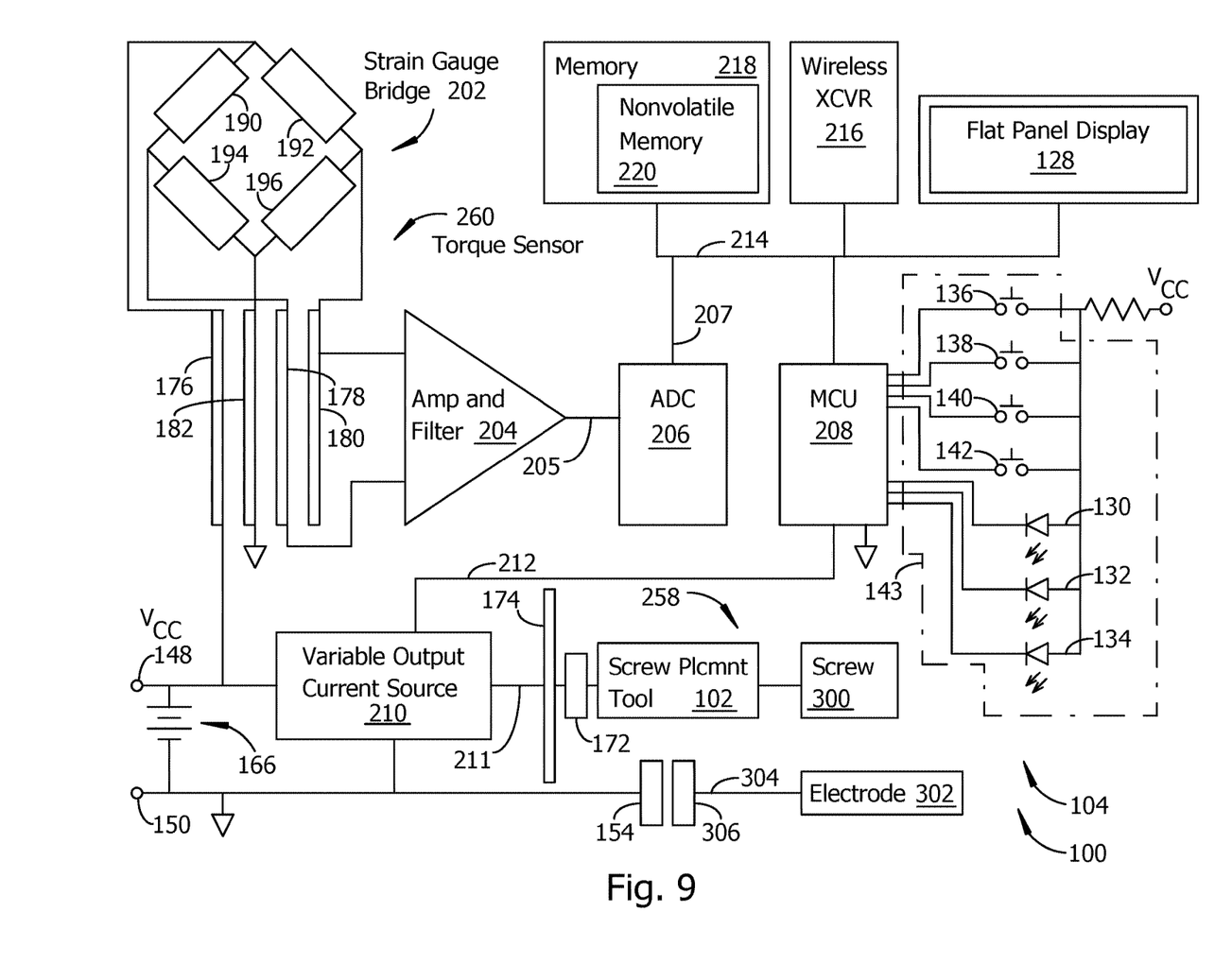
FIG. 9 is a schematic diagram of examples of components and electrical connections included in the intraoperative monitoring module of the previous figures.

Examples of electrical components and electrical connections in an IMM 104 included in an apparatus embodiment 100 are shown in an electrical schematic in FIG. 9. A torque sensor 260 includes an amplifier and filter circuit 204 receiving electrical signals from a strain gauge bridge 202. A low impedance, low voltage current return connection to the strain gauge bridge passes through the fifth slip ring 182 and is electrically connected to other current return points in the IMM 104, for example a common return terminal 150. In some embodiments the common return terminal 150 is one of the anti-rotation pins, for example the first anti-rotation pin 144. A bridge excitation voltage Vcc passes through the second slip ring 176 connected to an electric storage battery 166 and optionally to a positive power terminal 148. In some embodiments the positive power terminal 148 is another anti-rotation pin, for example the second anti-rotation pin 146.

The analog signal output 205 of the torque sensor 260, carried on an output of the amplifier and filter 204, is electrically connected to an input of an analog-to-digital converter (ADC). A digitized output 207 of the ADC 206 is electrically connected to an input of the microcontroller (MCU) 208. The digitized output 207 corresponds to numerical values of the analog output signal 205 from the torque sensor 260. In some embodiments 100 the ADC 206 and the MCU 208 are separate packaged devices and the ADC and MCU communicate with one another over an intervening data and command bus 214. In other embodiments the ADC and MCU are included on one integrated circuit.

The microcontroller 208 is configured to receive digitized strain gauge values from the strain gauge bridge 202, calibration values stored in a memory 218, and retrieve from the memory values of other parameters relating to conversion of strain to torque, and calculate a value of torque being applied to the screw 300 at the end of the screw placement tool attached to the IMM 104. Calculated values of torque are selectively displayed on the status display 128 and are optionally transmitted to external equipment through a wireless transceiver 216 in data communication with the MCU 208. Operating commands, network communication addresses for use by the wireless transceiver 216, calculated torque values, minimum and maximum values for preferred torque limits, stimulus current limits and values for evoked EMG measurements, calibration values, sequences of stored torque values for each fastener being placed, and other data and settings used by the MCU 208 are stored in the memory 218. Memory 218 connected for data communication with the MCU 208 includes nonvolatile memory 220.

The four strain gauges in the example of FIG. 9 are arranged in a "full-bridge" Wheatstone configuration. Resistors and other components may optionally be added to the strain gauge bridge 202 and/or the amplifier and filter 204 to provide temperature compensation, bridge nulling, and improve noise rejection. In some embodiments 100 the strain gauge bridge 202 is arranged as a "half bridge" with only two strain gauges.

The IMM 104 further includes a variable-output current source 210 configured to output a selected value of stimulus current in response to an electrical signal received over a current setpoint line 212 from the MCU 208. Upon command from the MCU 208, a selected magnitude of stimulus current for making an evoked EMG measurement is output over a continuous electrical current path 258 with low electrical resistance from the variable-output current source 210 to the screw 300 on the end of the screw placement tool 102. The stimulus current flows for a specified time duration from the variable-output current source 210 through the continuous electric current path 258 including an output 211 of the variable-output current source 210, the first slip ring 174, the spring-loaded pin 172 connected to the first slip ring, the screw placement tool 102, and the screw 300 at the end of the screw placement tool, and from the current path 259 into bone or other tissue in contact with the screw.

A common return connector 154 attached to the outer enclosure 108 is electrically connected to the common return terminal 150 for the variable-output current source 210. An electrode 302, for example a pin electrode coupled to an electrode connector 306 by an electrode cable 304, may be connected to the common return connector 154. The electrode 302 may be placed by a surgeon in tissue near a screw insertion path to provide a reference voltage for output of an accurately determined magnitude of stimulus current from the variable-output current source 210.

The IMM is capable of outputting the stimulus current concurrently with advancement of the screw into bone, measurement of corresponding torque values, comparison of torque values against stored torque limits, and display of information related to torque values, stimulus current values, and related torque and current limits. Concurrent, as used herein, is defined with respect to the actions and perceptions of a person interacting with an apparatus embodiment 100 and refers to events occurring within about one second of one another. An external EMG monitoring system, not included in the apparatus embodiments described herein, may detect a muscle response following injection of the stimulus current into bone through the IMM 104, screw placement tool 102, and screw 300. The surgeon performing the screw placement procedure may correlate the detected response from the EMG with values of torque and/or stimulus current presented on the status display 128 of the IMM 104.

When the external EMG monitoring system or a computer in data communication with the EMG monitoring system is capable of transmitting a signal corresponding to detection of a muscle response, the MCU 208 is optionally configured to receive the signal over the wireless transceiver 216. An alphanumeric, symbolic, and/or graphical indication of a muscle response may be displayed on the status display 128 by the MCU 208. The MCU 208 optionally illuminates one or more indicators (130, 132, 134) on the front side of the IMM in response to receiving a signal corresponding to detection of a muscle response. A surgeon may at their discretion continue advancing a screw into bone, determine that a screw is placed in bone with sufficient strength for secure screw retention, reverse the direction of screw rotation to remove the screw, choose another location or direction for screw insertion, or take other actions, according to a combination of torque values and stimulus current determined by and displayed on the IMM at the time of a detected muscle response.

Some embodiments of the IMM 104 are configured to display trend data, e.g. a pattern of increasing values or decreasing values over time, optionally relative to specified limits, from historical data stored in the IMM memory and/or data retrieved from an external storage system. Trend data may be stored, retrieved, and displayed for torque values, magnitude of stimulus current corresponding to a detected muscle response, for the entire duration of a procedure on one patient, for each individual screw placement, and for other bases for comparison.

Figure 2:
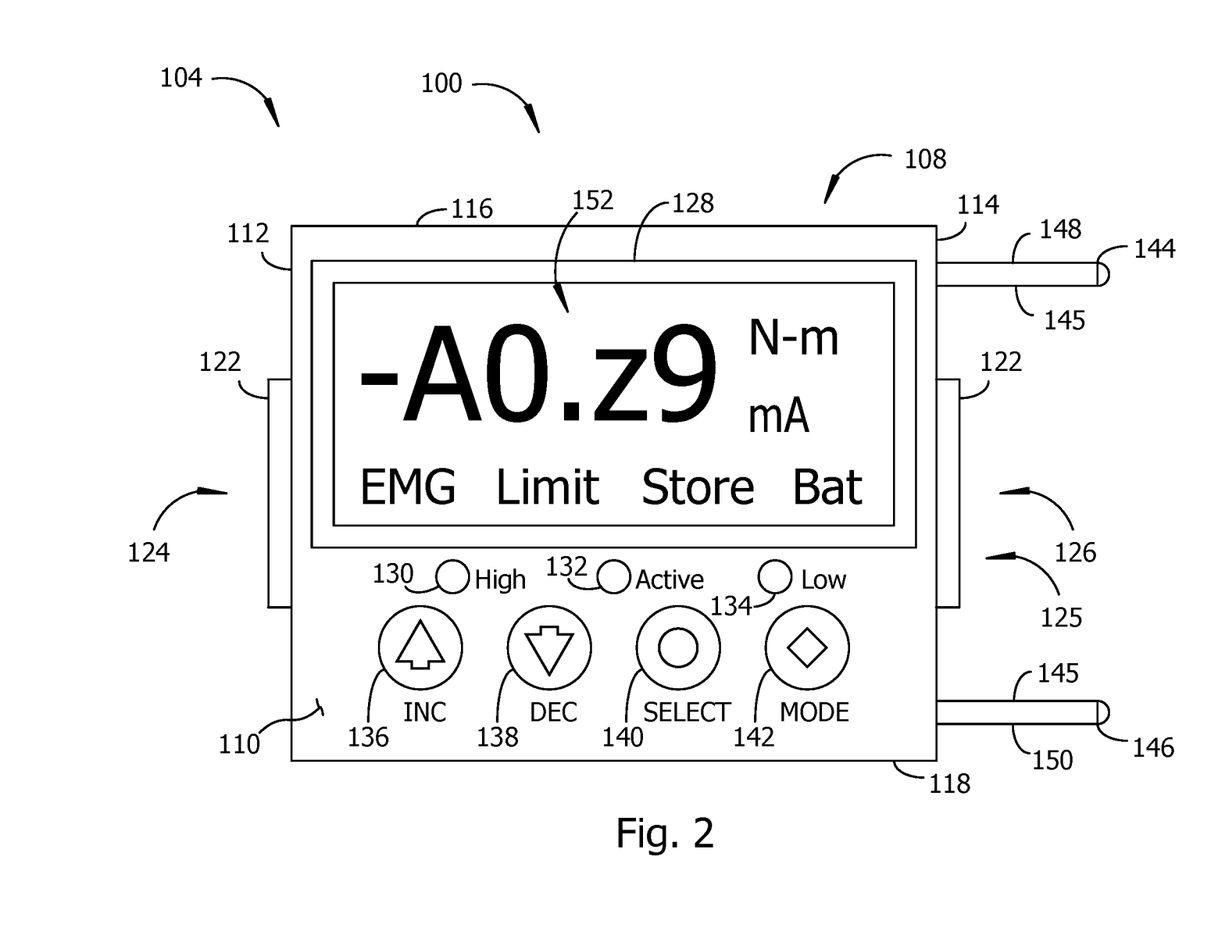
FIG. 2 shows a view toward a front side of an outer enclosure for the example intraoperative monitoring module of FIG. 1.
Figure 3:
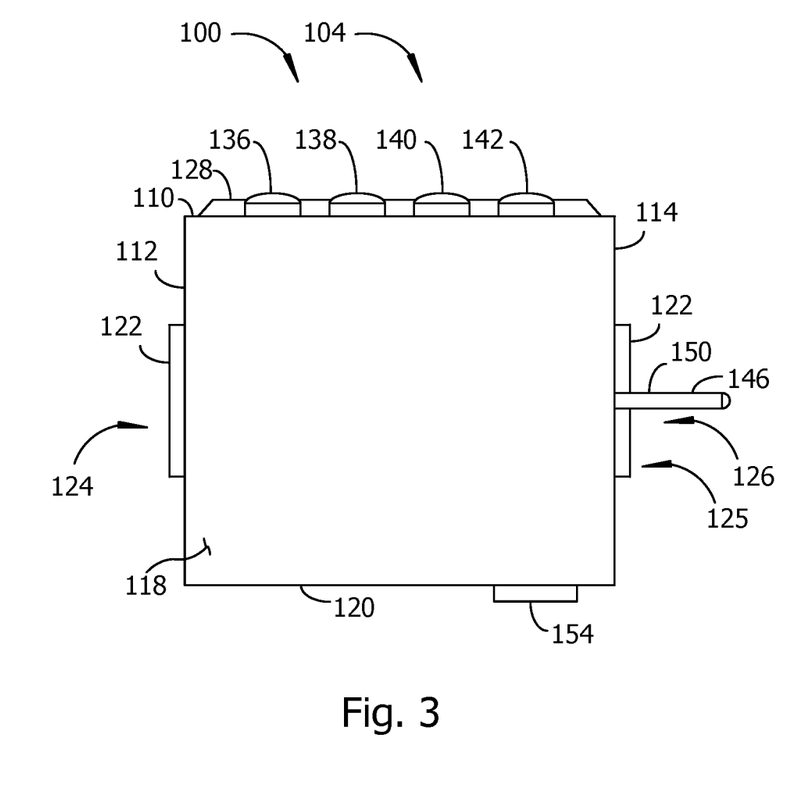
FIG. 3 shows a view toward a side wall of the outer enclosure for the example intraoperative monitoring module of FIGS. 1-2.
Figure 4:
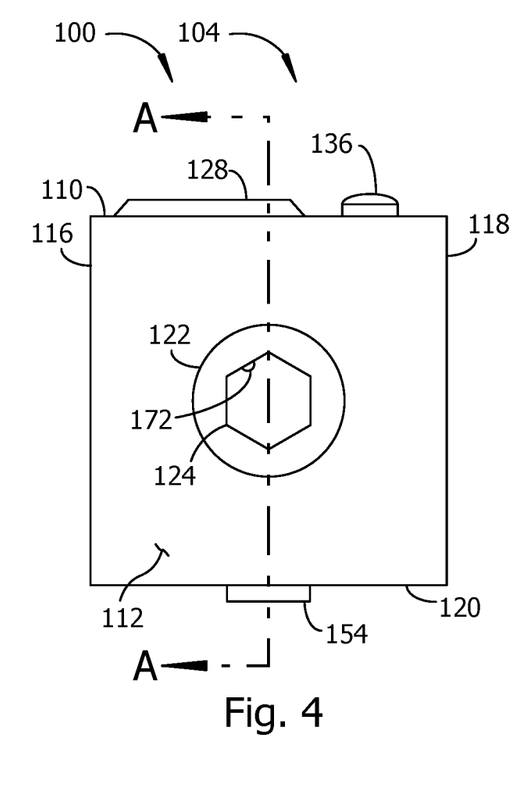
FIG. 4 shows a view toward another side wall of the outer enclosure for the example intraoperative monitoring module of FIGS. 1-3, further illustrating an example of an end of a tool receptacle having a tool socket for receiving a screw placement tool.

The IMM 104 preferably includes several switches and indicators for specifying data to be displayed on the status display, setting high and low limits for preferred torque values, setting a magnitude of stimulus current to be output from the IMM, and other controls and monitors useful to a surgeon during placement of screws and evaluation of screw attachment to bone. In the example of FIG. 9, four switches and three indicators are electrically connected to the MCU 208. Examples of labels for the switches and indicators are shown in FIG. 2. Labels on the front side optionally use different text than shown in the example of FIG. 2.

As an example of operation of an IMM 104, a first switch 136, labelled INC in the example of FIG. 2, may be activated by a surgeon to increment or increase a selected value. A second switch 138 labelled DEC may be activated to decrement or decrease a selected value. A third switch 140 labelled SELECT may be activated to select a displayed value for a parameter or make some other input choice, or to manually trigger output of a selected value of stimulus current from the variable-output current source 210. A fourth switch 142 labelled MODE may be activated to step through a set of operational choices.

Information 152 presented on the status display 128 includes text and/or graphics for guiding user selections with the switches. Examples of displayed text include, but are not limited to, "EMG", "Limit", Store", and "Bat". Examples of user selections made with the switches include, but are not limited to, setting upper and lower limits for torque values representative of acceptable screw placements, setting upper and lower limits for stimulus current corresponding to acceptable screw placements, breaches, weak bone, bone that is too hard, bone that is too soft, and/or other conditions (LIMIT), storing preferred limit values or measured values of torque or stimulus current to be used as limits or displayed for comparison (STORE), monitoring device status such as a low battery indicator (BAT), and setting stimulus current magnitude and limits (EMG).

Other examples of information 152 displayed on the status display 128 by the microcontroller 208 include, but are not limited to, a numerical torque value, a numerical stimulus current value, a unit applied to a displayed value, e.g. "N-M (Newton-meter) or "mA" (milliamp), graphical information such as trend lines and/or bar graphs, event identification such as a record number of a screw being placed during a procedure, and so on. For example, the MODE switch 142 may be depressed until EMG is shown on the status display to prepare the IMM for outputting a stimulus current for an EMG measurement. A value of stimulus current selected by operation of the INC switch 136 and DEC switch 138 may be output under command of the surgeon by activation of the SELECT key.

Indicators on the front side 110 optionally include any one or more of a first indicator 130 (HIGH limit indicator), optionally activated by the MCU 208 to alert the surgeon to a high limit being exceeded, a second indicator 132 (ACTIVE), optionally activated by the MCU to indicate initiation of an event such as output of a stimulus current, and a third indicator 134 (LOW limit indicator), optionally activated by the MCU to indicate a low limit being passed. An illuminated indicator is an example of an activated indicator. Some operational conditions optionally activate more than one indicator, for example to alert a user to an error condition in the IMM, a disallowed button activation, and so on. Alternative embodiments 100 optionally include a different number of switches and indicators than are shown in the examples of FIG. 2 and FIG. 9, and optionally use different switch and indicator labels than shown in the example figures.

Figure 10:
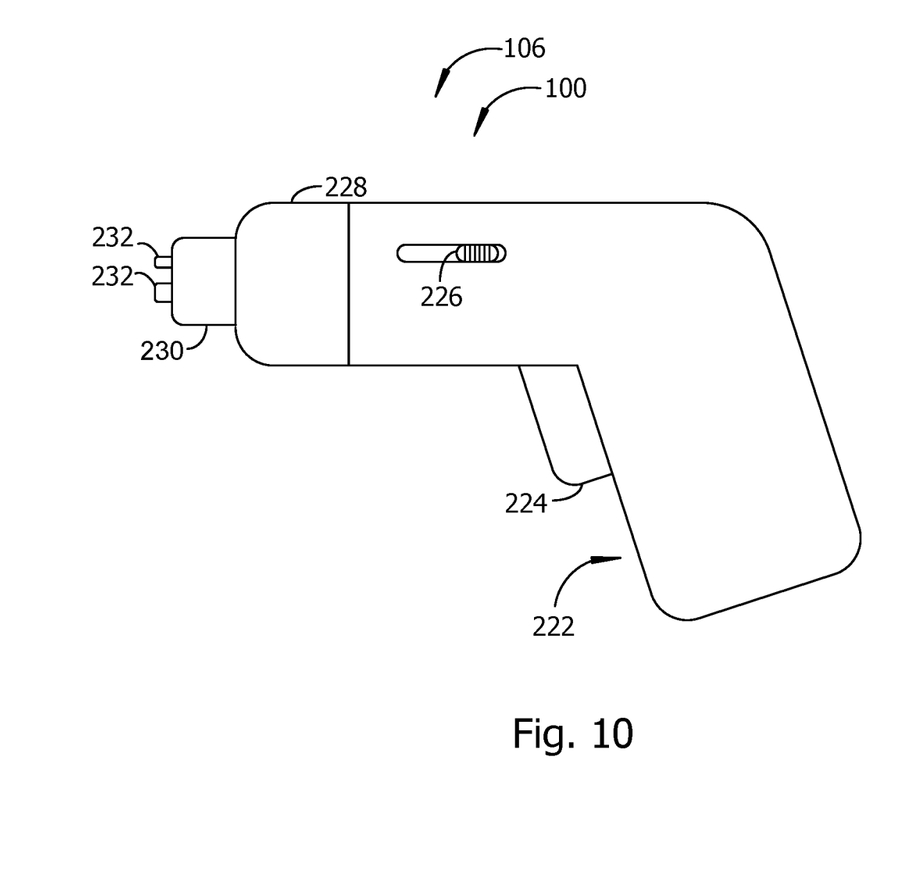
FIG. 10 shows a view toward a side of the example motor housing from FIG. 1.
Figure 11:
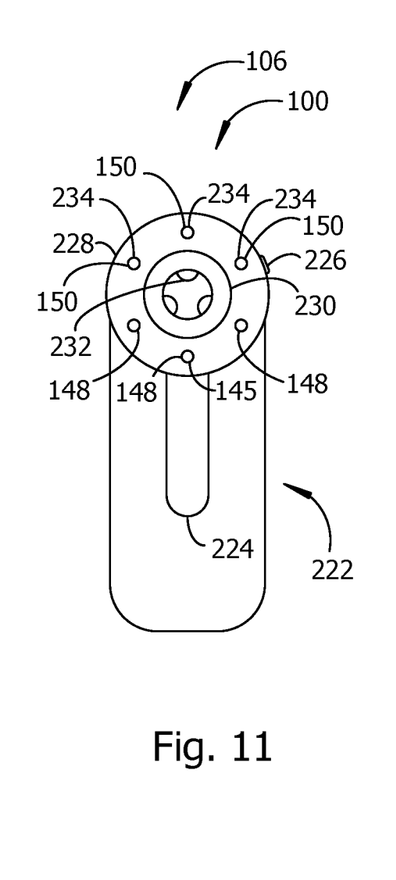
FIG. 11 shows a view toward a rotatable chuck on the example motor housing from FIG. 10.

Examples of a motor housing 106 included with some apparatus embodiments 100 are shown in FIGS. 10, 11, 12, 13, and 14. FIGS. 10 and 11 illustrate an example of a motor housing 106 with an angled hand grip 222 and a chuck 230 having one or more adjustable jaws 232 for gripping a tool receptacle 122 having a drive coupling 125 implemented as a post, such as the example IMM 104 of FIG. 6 having a hexagonal post 156. Tightening the adjustable clamp jaws 232 against the flat sides of the hexagonal post 156 by rotating the chuck 230 holds the IMM firmly against the motor housing with the tool receptacle 122 rotatable by the motors in the motor housing and the outer enclosure 108 stationary with respect to the hand grip on the motor housing. The motor housing 106 optionally includes an adjustable torque ring 228 for setting a maximum amount of output torque from the motors in the motor housing. The motor housing is optionally formed with at least one, and possibly several pin receptacles 234 configured to receive the anti-rotation pins (144, 146) on the IMM 104. Spacing pin receptacles at intervals around the chuck provides for attachment of the IMM to the motor housing at a selected viewing angle determined by the position of the selected pin receptacle.

Figure 12:
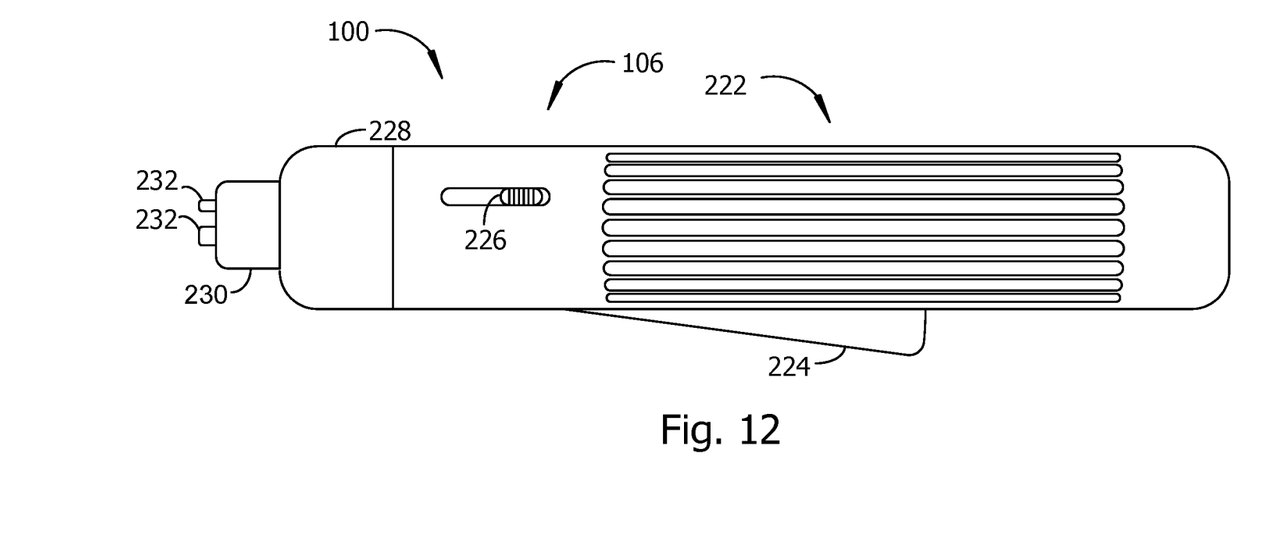
FIG. 12 illustrates an alternative arrangement of a hand grip and speed control switch for a motor housing in accord with an embodiment.
Figure 13:
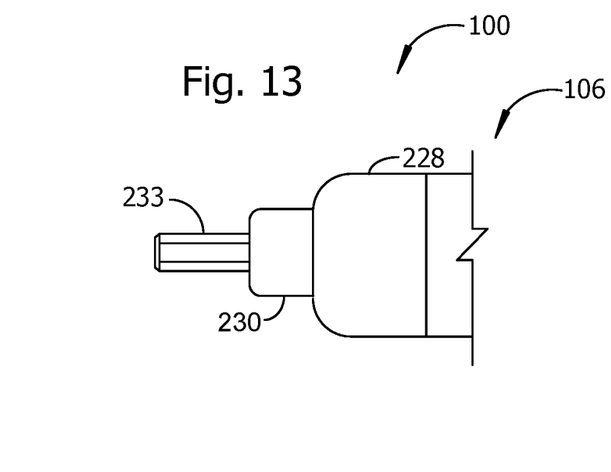
FIG. 13 shows a partial side view of an example chuck including a screw driver shank.
Figure 14:
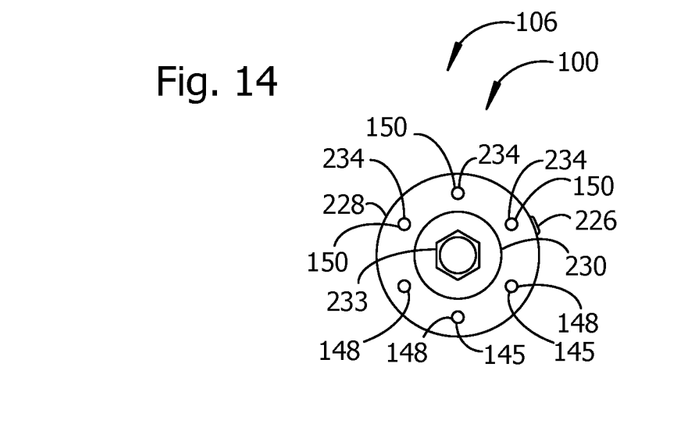
FIG. 14 shows a view toward an end of the shank from the example chuck of FIG. 13.

FIG. 12 show an example of a hand grip 222 on an approximately cylindrical motor housing 222. The chuck 230 in the example of FIG. 12 has clamp jaws 232 similar to those on the motor housing in the examples of FIGS. 10-11. Any of the previously described motor housings optionally replace the chuck with adjustable jaws with a chuck having a hexagonal drive shaft 233 shaped to engage with an IMM 104 having a drive coupling 125 implemented as a hexagonal socket 126. An example chuck 230 having an Some embodiments of the IMM 104 include an internal electrical storage battery 166 as suggested in the examples of FIG. 7 and FIG. 9. Some embodiments of an IMM are configured to receive electrical power from an external source. For example, in some embodiments 100 the anti-rotation pins (144, 146) also function as electrical power connection pins and are electrically connected to the positive power terminal 148 and the common return terminal 150 on the IMM. The positive power terminal 148 may also be referred to as the Vcc terminal 148. At least two of the pin receptacles 234 on some embodiments of the motor housing 106 are configured as a positive power terminal 148 and a common return terminal 150 for supplying electrical power from a battery in the motor housing (not illustrated) to circuit components in the IMM. When the battery 166 in the IMM is a rechargeable battery, the motor housing 106 optionally includes a battery charger configured to recharge the battery in the IMM through the Vcc (148) and common return (150) terminals on the IMM.

Figure 15:
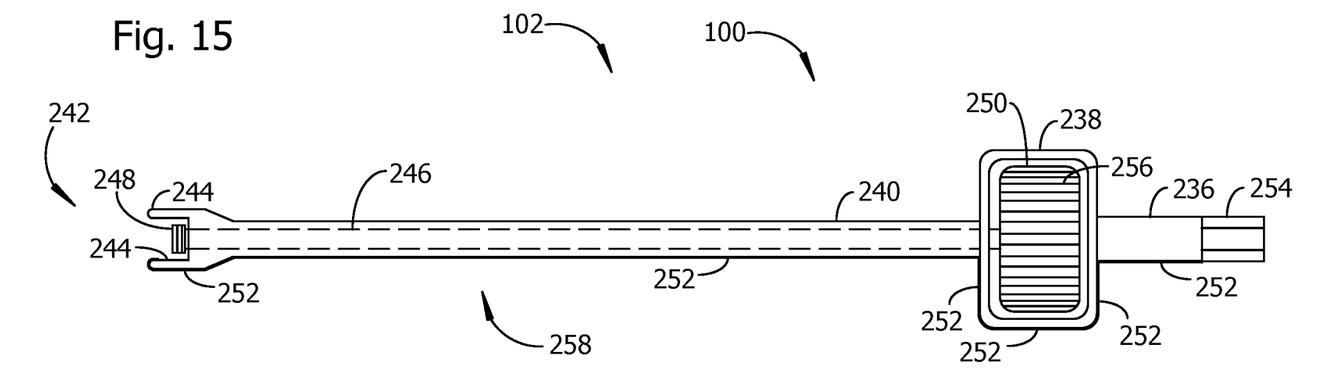
FIG. 15 shows a side view of an example screw placement tool configured as a screw driver for tulip head screws used in orthopedic procedures.
Figure 16:
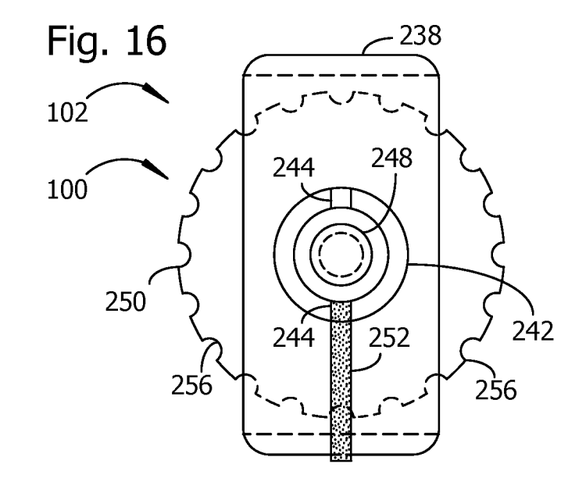
FIG. 16 shows a view toward the screw engaging end of the example screw placement tool of FIG. 1 and FIG. 15.
Figure 17:
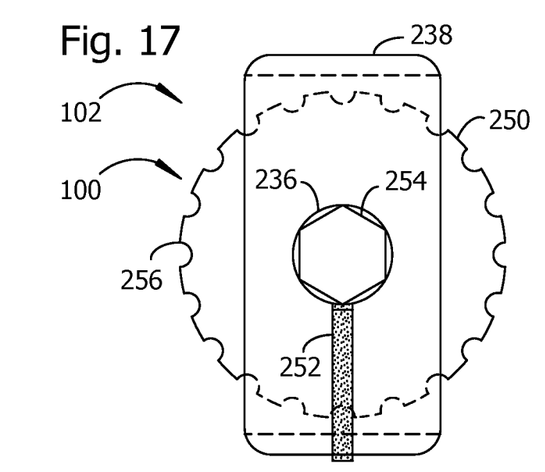
FIG. 17 shows a view toward the screw driver shank of the example screw placement tool of FIG. 1 and FIGS. 15-16.

FIGS. 15-17 show views of an example screw placement tool 102 included with some apparatus embodiments 100. The example screw placement tool in FIGS. 15-17 is configured as a screw driver for tulip head screws used in some orthopedic procedures. A screw driver shank 236 is strongly attached to a thumbwheel cage 238. The screw driver shank 236 optionally terminates in a hexagonal end 254 to oppose slippage of the screw driver shank in the chuck of the motor housing. A hollow sleeve 240 is strongly attached to the thumbwheel cage on a side opposite the screw driver shank 236. When configured for driving a tulip head screw, the hollow sleeve 240 terminates in tines 244 projecting outward from a screw engaging end 242 of the hollow sleeve.

The tines 244 are positioned to engage corresponding slots or channels formed along the sides of the head of a tulip head screw.

A shaft 246 passes through the central aperture of the hollow sleeve 240. An end of the shaft 246 is attached to a thumbwheel 250 positioned inside the thumbwheel cage 238. A threaded end 248 of the shaft 246 opposite the thumbwheel 250 is configured to engage with internal threads formed in an aperture in the head of a tulip head screw. Rotating the thumbwheel in a first direction engages the threaded end 248 with the threads in the tulip head screw and draws the tines 244 into firm contact with the channels in the screw head, opposing rotation of the screw relative to the hollow sleeve, thumbwheel cage, and drive shank. Rotating the thumbwheel in a second direction opposite the first direction disengages the threaded end 248 from the screw head, allowing the screw to separate from the tines 244. Finger grips 256 formed on the thumbwheel 250 make the thumbwheel easier to turn.

The screw placement tool 102 forms part of the continuous electrical current path 258 from the IMM 104 to the tip of a screw being placed in bone. However, in some embodiments parts of the screw replacement tool may optionally be made from materials with sufficiently high electrical resistance to impede current flow output from an IMM 104 during an evoked EMG measurement, possibly decreasing the accuracy of the measurement. A screw placement tool therefore optionally includes an electrical conductor 252 to establish a low-impedance current path along the screw driver shank 236, thumbwheel cage 238, hollow sleeve 240, and at least one of the tines 244. In some embodiments the electrical conductor 252 is affixed to the screw placement tool along the current path. In other embodiments the electrical conductor 252 is an integrally-formed part of the screw placement tool. The electrical conductor 252 is preferably positioned on a tine 244 to establish good electrical contact with a screw head held against the tine by the threaded end of the shaft 246.

Unless expressly stated otherwise herein, ordinary terms have their corresponding ordinary meanings within the respective contexts of their presentations, and ordinary terms of art have their corresponding regular meanings.

What is claimed is:

1. An intraoperative monitoring apparatus, comprising:
   an outer enclosure;
   a tool receptacle rotatably coupled to said outer enclosure, comprising:
      a tool socket;
      a torque sensor attached to said tool receptacle; and
      a drive coupling at an end of said tool receptacle opposite said tool socket;
   a variable-output current source electrically connected to a contact pin attached to said tool receptacle;
   a microcontroller electrically connected to said torque sensor and said variable-output current source, said microcontroller configured to determine a value of current from said variable-output current source and a value of rotational torque from an output of said torque sensor;
   a screw placement tool comprising a screw engaging end and a screw driver shank opposite said screw engaging end;
   an electrical conductor affixed to said screw placement tool, said electrical conductor extending from said screw engaging end to said screw driver shank;
   said tool receptacle further comprising:
      a contact pin electrically connected to said variable-output current source, said contact pin extending into said tool socket to contact said electrical conductor;
      a slip ring affixed to an outer surface of said tool receptacle, said slip ring electrically connected to said contact pin; and
      a spring contact positioned in said outer enclosure to establish an electrical connection between said slip ring and said variable-output current source.

2. The intraoperative monitoring apparatus of claim 1, further comprising:
   an anti-rotation pin extending outward from said outer enclosure; and
   a motor housing configured for attachment to said drive coupling and said outer enclosure, said motor housing formed with a pin receptacle positioned to receive said anti-rotation pin.

3. The intraoperative monitoring apparatus of claim 2, wherein said outer enclosure is integrally formed with said motor housing.

4. The intraoperative monitoring apparatus of claim 1, wherein said screw driver shank engages said tool socket with a close sliding fit.

5. The intraoperative monitoring apparatus of claim 1, said torque sensor further comprising:
   a strain gauge bridge comprising two strain gauges; and
   an amplifier and filter electrically connected to said strain gauge bridge.

6. The intraoperative monitoring apparatus of claim 5, said strain gauge bridge comprising an additional two strain gauges.

7. The intraoperative monitoring apparatus of claim 5, wherein a strain-sensing axis for each of said two strain gauges is positioned at an angle of 45 degrees to a rotational axis of said tool receptacle.

8. The intraoperative monitoring apparatus of claim 5, further comprising an analog-to-digital converter having an input electrically connected to an output of said amplifier and filter and a digitized output electrically connected to said microcontroller.

9. The intraoperative monitoring apparatus of claim 1, further comprising:
   a memory connected for data communication with said microcontroller; and
   a high limit indicator on a front side of said outer enclosure,
   wherein said microcontroller is configured to activate said high limit indicator when said value of rotational torque exceeds a high torque limit value stored in said memory.

10. The intraoperative monitoring apparatus of claim 9, wherein said microcontroller is configured to store in said memory said value of rotational torque as said high torque limit value.

11. The intraoperative monitoring apparatus of claim 9, further comprising a low limit indicator on said front side, wherein said microcontroller is configured to activate said low limit indicator when said value of rotational torque is less than a low torque limit value stored in said memory.

12. The intraoperative monitoring apparatus of claim 9, wherein said microcontroller is configured to store in said memory said value of rotational torque as said low torque limit value.

13. The intraoperative monitoring apparatus of claim 1, wherein said microcontroller is configured to determine said value of rotational torque concurrently with said variable-output current source outputting a value of stimulus current communicated from said microcontroller.

14. The intraoperative monitoring apparatus of claim 1, wherein said microcontroller is configured to compare said value of rotational torque to a torque limit concurrently with said variable-output current source outputting a value of stimulus current communicated from said microcontroller.

15. The intraoperative monitoring apparatus of claim 1, wherein said tool receptacle includes a magnet positioned to hold a screw placement tool inserted into said tool socket.

16. The intraoperative monitoring apparatus of claim 1, further comprising a status display attached to said outer enclosure, said status display connected for data communication with said microcontroller.

* * * * *